US00PP17096P2

(12) United States Plant Patent
Lemon

(10) Patent No.: US PP17,096 P2
(45) Date of Patent: Sep. 12, 2006

(54) ***GERANIUM* PLANT NAMED 'MAESTRO WHITE SPLASH'**

(50) Latin Name: *Pelargonium×hortorum*
Varietal Denomination: Maestro White Splash

(75) Inventor: David G. Lemon, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 11/177,054

(22) Filed: Jul. 8, 2005

(51) Int. Cl.
*A01H 5/00* (2006.01)

(52) U.S. Cl. ..... Plt./325

(58) Field of Classification Search ..... Plt./325
See application file for complete search history.

*Primary Examiner*—Kent Bell
(74) *Attorney, Agent, or Firm*—The Webb Law Firm

(57) ABSTRACT

'Maestro White Splash' is a new variety of *geranium* having free flowering and white petals with intensely hot pink eyes.

1 Drawing Sheet

Botanical classification: *Pelargonium×hortorum.*
Varietal denomination: 'Maestro White Splash'.

BACKGROUND OF THE INVENTION

The present invention comprises a new and distinct cultivar of *Pelargonium×hortorum* known by the varietal name 'Maestro White Splash'. The new variety was discovered in Lompoc, Calif. The new variety is a result of cross breeding 'Americana White Splash' (female parent) (U.S. Plant Pat. No. 9,317) and 'Patriot Light Pink' (male parent) (U.S. Plant Pat. No. 10,484). The purpose of the breeding program was to introduce a compact *geranium* more suitable for tight greenhouse spacing. The new variety is similar in flower color to its female parent, but has a more compact and spreading habit with early flowering. The new variety exhibits a different flower color than its male parent. 'Maestro White Splash' is also more free and early flowering with a compact habit and has good repeat blooming when compared to other varieties known to the breeder. The new variety was first asexually reproduced by cuttings in Connellsville, Pa. The new variety has been trial and field tested and has been found to retain its distinctive characteristics and remain true to type through successive propagations.

The new variety was grown in a 4" pot with fertilizer at 200 ppm nitrogen. The new variety exhibits developed roots at 17 days at an average temperature of 21° C. and has a response time of seven weeks from a rooted cutting to flowering in a 10 cm. container.

DESCRIPTION OF THE DRAWING

The accompanying photographic drawing illustrates the new variety, with the color being as nearly true as is possible with color illustrations of this type.

DESCRIPTION OF THE PLANT

Figure 1:
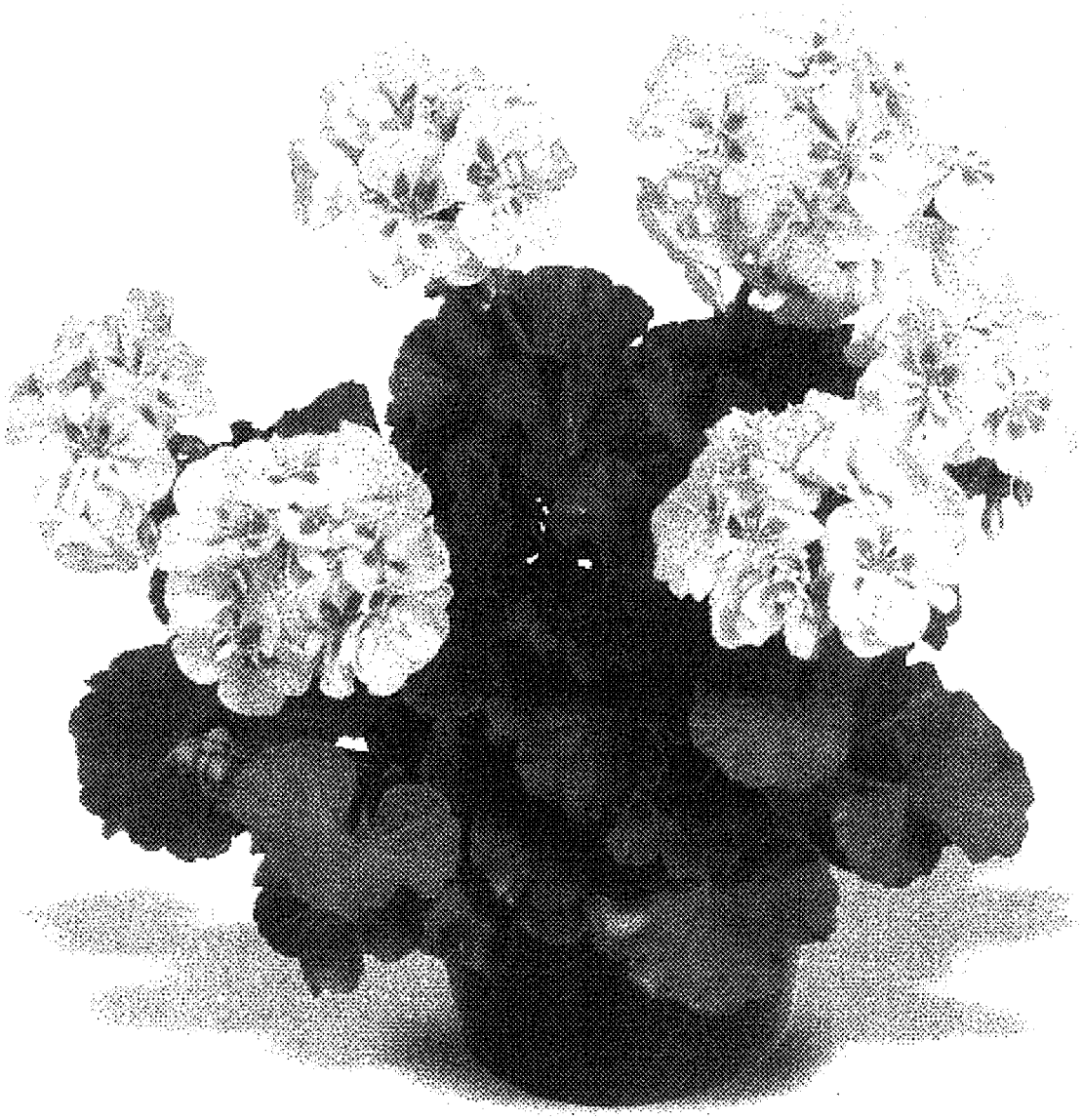

The following detailed description sets forth the characteristics of the new cultivar. The data which defines these characteristics were collected by asexual reproductions carried out in Connellsville, Pa. The color readings were taken indoors under 200–220 foot candles of cool white fluorescent light. The new variety was eight weeks from a rooted cutting when described. Color references are primarily to the 1966 R.H.S Colour Chart of The Royal Horticultural Society of London.

PLANT

Market class: Zonal.
Time to initiate roots: Approximately 5–7 days at about 21° C.
Time to develop roots: Approximately 17 days at about 21° C.
Time to produce a finished flowering plant from a rooted cutting: About 7 weeks in a 10 cm. container.
Rooting habit: Normal.
Form (e.g., spreading, mounded, symmetrical): Mounded.
Height from media surface to top of foliage: 11.0–12.0 cm.
Height from media surface to top of flowers: 19.5–21.5 cm.
Plant diameter: 26.0–27.0 cm.
Strength: No artificial support needed.
Branching habit: Free branching.
Stem:
- *Main stem length.*—9.5 cm.
- *Diameter.*—0.8 cm.
- *Color.*—Green Group 137C.
- *Texture.*—Leathery.
- *Pubescence.*—Light.
- *Internode length.*—1.7–3.0 cm.

Lateral branches:
- *Length.*—Primary: 7.8–8.2 cm. Secondary: Too young to measure.
- *Diameter.*—Primary: 0.6 cm. Secondary: Too young to measure.
- *Internode length.*—2.2–3.2 cm.
- *Texture.*—Leathery.
- *Pubescence.*—Light.
- *Color.*—Green Group 137C.

Foliage:
- *Arrangement (e.g., alternate, single).*—Alternate.
- *Stipules.*—Size: 0.8 cm.×0.8–0.9 cm. Quantity: 2 at each node. Color: Green Group 137C.
- *Zone.*—None present.
- *Size of leaf.*—Length: From attachment to petiole: 4.8–5.2 cm. Width: 8.6–9.0 cm.

*Shape of leaf* (*generally*).—Reniform with a cordate base.
*Shape of apex.*—Rounded; curved.
*Shape of base.*—Cordate.
*Texture.*—Leathery.
*Margin type.*—Crenate with a stalked leaf attachment.
*Pubescence.*—Upper surface: Light. Lower surface: Light.
*Color.*—Young leaves: Upper surface: Green Group 137B. Lower surface: Green Group 137C. Mature leaves: Upper surface: Green Group 137A. Lower surface: Green Group 137C.
*Petiole.*—Length: 5.2–5.7 cm. average. An old leaf has a petiole length of 7.5 cm. Diameter: 2–2.5 mm. Color: Yellow-Green Group 146B.
*Veins.*—Venation type: Palmate. Color: Upper surface: Yellow-Green Group 148B, when visible. Lower surface: Yellow-Green Group 148B.

INFLORESCENCE

Bud:
*Stage of development when bud characteristics determined.*—One floret just opening at sepal tips.
*Shape of cluster.*—Oval — ellipse.
*Diameter of cluster.*—2.3–2.4 cm.
*Number of buds per cluster.*—16–20 (more present as the plant matures).
*Shape of individual bud.*—Ellipse — pointed at apex.
*Length of individual bud.*—Just prior to opening: 0.9–1.0 cm.
*Width of individual bud.*—0.6–0.65 cm.
*Color note.*—As bud pushes beyond sepals and prepares to open, the petal's exposed surface appears to be Orange-White Group 159C and the upper petal surface appears to be Red-Purple Group 62C-D.

Natural flowering season at specified location(s): Forced in a greenhouse, so there is no specific season.
Blooming habit: Continuous and free-flowering.
Umbel diameter of a mature flower: 10 cm.
Umbel depth: 5.8–5.9 cm.
Borne: Umbel, flowers on pedicel, pedicel on peduncle. Also, the three lower petals are grouped together and then there is a space and two upper petals.
Lastingness of an individual flower: 10–14 days.
Florets:
*Form.*—Flat (as the plant matures) and slightly cupped.
*Number per umbel.*—23–32.
*Diameter.*—4.7–5.2 cm.
*Depth.*—None at the mature stage to 2.7 cm. for a new floret.

Petals: Color: Upper surface: White with a blush pink tint. The closest white is White Group 155D. There is an illusion of tint to resemble a pale Red-Purple Group 69C. The veins from base to eye are Red-Purple Group 64A. The blotch (eye) covers the width of the petal at the base prior to narrowing for attachment. It then tapers to a central point just under half of the length of the petal. The blotch (eye) is smaller on lower petals and Red-Purple Group 66B. The lower petals do not have blotch extending the width of the petal base. Near the edge of the blotch, the color resembles Red-Purple Group 63B. Older flowers have less blush. The lower petals have no veining. Lower surface: The upper and lower petals are White Group 155D. The upper petals have veining from the base to ½ distance of the petal. The vein is Red-Purple Group 67A at its darkest point and is overcome by white to resemble Red-Purple Group 68C & D.
*Shape.*—Similar to rounded heart shape — inverted tear drop.
*Length.*—2.0–2.9 cm.
*Width.*—1.7–2.5 cm.
*Apex shape.*—Rounded.
*Base shape.*—Pointed — like an arrow.
*Margin.*—Entire.
*Number per floret.*—5–8 petals.
*Texture.*—Smooth; delicate.

Tonality from a distance: White flowers with intensely hot pink eyes on all petals. The white looks as though it reflects the hot pink from the eye giving an illusion of the faintest pink in petals atop a medium green mound.
Petaloids:
*Quantity.*—1–5.
*Shape.*—Generally irregular, tubular, partial petals crinkled. Curved ½ petals longitudinally, curvy anther or stamen-like structures and various shapes to these are acting as filaments.
*Color* (*upper and lower surface*).—White Group 155D (brighter) with a tint of Red-Purple Group 69A.
*Color* (*upper and lower surface*).—White Group 155D (brighter) with a tint of Red-Purple Group 69A.
*Length.*—0.7–1.8 cm.
*Width.*—0.15–0.3 cm.
Pedicel:
*Length.*—2.9–3.1 cm.
*Diameter.*—1.5 mm.
*Color.*—Yellow-Green Group 144B is best to describe.
Peduncle:
*Length.*—11.8–15.0 cm. — most are between 11.8–14.5 cm.
*Diameter.*—0.4 cm.
*Texture.*—Leathery.
*Color.*—Yellow-Green Group 144A.
Sepal:
*Number.*—5.
*Pubescence.*—Moderate.
*Shape.*—Lanceolate.
*Width.*—0.2–0.4 cm.
*Length.*—0.9–1.2 cm.
Fragrance: None present.
Disease resistance: None observed.
Temperature tolerance: Average — nothing out of the ordinary.
Drought tolerance: None observed, average.

REPRODUCTIVE ORGANS

Stamens:
*Number* (*per flower*).—5–8 stamens.
*Filament.*—Length: 7–8 mm (0.7–0.8 cm.). Color: White Group 155D with Red-Purple Group 63C, tipped in Red-Purple Group 63A.
*Anthers.*—Shape: Rectangular, curved backward. Length: 1.9–2.0 mm (0.019–0.02 cm.). Color: The back of the anther is Red-Purple Group 63C, the rest is covered in pollen.
*Pollen.*—Color: Orange-Red 31A. Amount (generally): Lots of pollen.
Pistils:
*Number.*—One.
*Length.*—0.6 cm.
*Style.*—Length: 0.3 cm. Color: Orange-White Group 159C.
*Stigma.*—Shape: Splits into 5 arms. Color: Red-Purple Group 62C; tipped in Red-Purple Group 63A. Size: 0.3 cm.

*Ovaries.*—Position: Superior Pubescence: Present. Length: 2.5 mm (0.25 cm.). Width: 1.8–2.0 mm wide (0.18–0.02 cm.).

*Color.*—Green Group 138B.

I claim:

1. A new and distinct variety of *geranium* plant named 'Maestro White Splash' as described and illustrated.

* * * * *